United States Patent [19]

Rubin et al.

[11] Patent Number: 5,860,929
[45] Date of Patent: Jan. 19, 1999

[54] FRACTIONAL MOVING BLOOD VOLUME ESTIMATION WITH POWER DOPPLER ULTRASOUND

[75] Inventors: Jonathan M. Rubin; Ronald S. Adler; J. Brian Fowlkes, all of Ann Arbor, Mich.; Ray Steven Spratt, San Jose, Calif.

[73] Assignee: The Regents of the University of Michigan, Ann Arbor, Mich.

[21] Appl. No.: 657,897

[22] Filed: Jun. 7, 1996

[51] Int. Cl.$^6$ .................................................. A61B 8/06
[52] U.S. Cl. .......................................................... 600/454
[58] Field of Search ........................... 128/661.07–661.1, 128/916; 73/861.25; 600/454–458

[56] References Cited

U.S. PATENT DOCUMENTS 5,233,994   8/1993   Schmulewitz ...................... 128/661.08
5,471,990  12/1995   Thirsk ................................. 128/661.09
5,474,073  12/1995   Schwartz et al. ..................... 128/661.1

OTHER PUBLICATIONS

Adler et al., "Dopler Ultrasound Color Flow Imaging in the Study of Breast Cancer: Preliminary Findings," Ultrasound in Medicine and Biology, 1990, vol. 16, No. 6, pp. 553–559.

Adler et al., "Ultrasonic Estimation of Tissue Perfusion: A Stochastic Approach," Ultrasound in Medicine and Biology, 1995; vol. 21, No. 4, pp. 493–500.

Anderson et al., "CT Techniques, "Computed Body Tomography with MRI Correlation, 2nd Edition, Lee et al, editors, New York, NY: Raven, 1989; pp. 46–50.

Atkinson et al., "Random Noise in Ultrasonic Echoes Diffracted by Blood," Journal of Physics A: Mathematical Nuclear and General, 1974, vol. 7, No. 11, pp. 1293–1302.

Axel, "Cerebral Blood Flow Determination by Rapid–Sequence Computed Tomography: A Theoretical Analysis," Radiology, 1980, vol. 137, No. 3, pp. 679–686.

Bamber et al., "Parametric Imaging of Tissue Shear and Flow using B–Scan Decorrelation Rate," (Abstract), Journal of Ultrasound Medicine, 1988; vol. 7, No. 10, pp. S135–S136.

Berman et al., "Sonographic Evaluation of Acute Intrascrotal Pathology," American Journal of Roentgenology, Apr. 1996, vol. 166, pp. 857–861.

Bourne et al., "Transvaginal Colour Flow Imaging: A Possible New Screening Technique for Ovarian Cancer," British Medical Journal, 1989, vol. 299, pp. 1367–1370.

Bragg et al., "Radiologic Techniques in Cancer," Cancer: Principles & Practice of Oncology, 3rd Edition, Devita, Jr. et al., editors, Philadelphia, PA:Lippincott, 1989, pp. 440–464.

Brenner et al., "The Renal Circulations," The Kidney, 3rd Edition, Brenner et al., editors, Philadelphia, PA:Saunders, 1986,pp. 114–118.

(List continued on next page.)

Primary Examiner—Francis Jaworski
Attorney, Agent, or Firm—Arnold, White & Durkee

[57] ABSTRACT

A method for quantitatively estimating the amount of tissue that contains moving blood using power Doppler ultrasound. A region of interest is identified from a frozen image (i.e., a snapshot screen display created by displaying the last real-time image for a given scan). The region of interest is specified by using a pointing device (e.g., a mouse). An object that contains one hundred percent blood flow and is located at the same depth as the region of interest, but not necessarily inside the region of interest, is identified and the corresponding power noted and designated as the reference power level. The display is adjusted to show the one hundred percent blood flow vessel in a designated color (such as, for example, green) and all other power levels are normalized to the reference power level. The fractional blood volume is quantitatively estimated by summing the normalized Doppler power levels in a region of interest and dividing the sum by the number of pixels in region of interest. The numerical result for the specified region of interest may be shown on the display of the ultrasound scanner.

20 Claims, 3 Drawing Sheets

OTHER PUBLICATIONS

Burns et al., "Power Doppler Imaging Combined with Contrast–Enhancing Harmonic Doppler: New Method for Small–Vessel Imaging," (Abstract), Radiology, 1994, vol. 13(P), p. 366.

Burns, "Hemodynamics," Clinical Applications of Doppler Ultrasound, Taylor et al., editors, Nw York, NY: Raven, 1988, pp. 46–75.

Carson et al., "Approximate Quantification of Detected Fractional Blood Volume and Perfusion from 3–D Color Flow and Doppler Power Signal Imaging," Levy et al., editors, Procedings of the 1993 IEEE Ultrasonics Symposium, Baltimore, Maryland, Oct. 31–Nov. 3, 1993; Catalog No. 93CH3301–9, vol. 2, pp. 1023–1026.

Castagnone et al., "Color Doppler Sonography in Graves' Disease: Value in Assessing Acitivity of Disease and Predicting Outcome," American Journal of Roentgenology, Jan. 1996, vol. 166, pp. 203–207.

Coley et al., "Acute Testicular Torsion: Comparison of Unenhanced and Contrast–Enhanced Power Doppler US, Color Doppler US, and Radionuclide Imaging," Radiology, 1996, vol. 199, No. 2, pp. 441–446.

Cosgrove et al., Breast Diseases: Color Doppler US in Differential Diagnosis, Radiology, 993, vol. 189, pp. 99–104.

Cosgrove et al., "Color Doppler Signals from Breast Tumors," (work in progress), Radiology, 1990, vol. 17, pp. 175–180.

Dixon et al., "Colour Doppler Ultrasonography Studies of Benign and Malignant Breast Lesions," The British Journal of Surgery, 1992, vol. 79, pp. 259–260.

Downey et al., "Three–Dimensional Powre Doppler Detection of Prostatic Cancer," American Journal of Roentgenology, 1995, vol. 165, p. 741.

Downey et al., "Vascular Imaging with a Three–Dimensional Power Doppler System," American Journal of Roentgenology, 1995, vol. 165, pp. 665–668.

Dymling et al., "Measurement of Blood Perfusion in Tissue Using Doppler Ultrasound," Ultrasound in Medicine and Biology, 1991, vol. 17, No. 5, pp. 433–444.

Faran, "Sound Scattering by Solid Cylinders and Spheres," The Journal of the Acoustical Society of America, 1951, vol. 23, No. 4, pp. 405–418.

Folkman, "Tumor Angiogenesis," Advances in Cancer Research, vol. 43, Klein et al, editors, Academic Press, Inc., 1985, pp. 175–203.

Hottinger et al., "Blood Flow Measurement Using the Attenuation–Compensated Volume Flowmeter," Ultrasonic Imaging, 1979, vol. 1, No. 1, pp. 1–14.

Huber et al., "Breast Tumors: Computer–Assisted Quantitive Assessment with Color Doppler US," Radiology, 1994, vol. 192, No. 3, pp. 797–801.

Kabas et al., "Intraoperative Perfusion Contrast Echocardiography; Initial Experience During Coronary Artery Bypass Grafting," The Journal of Thoracic and Cardiovascular Surgery, 1990, vol. 99, No. 3, pp. 536–542.

Kedar et al., "Automated Quantification of Color Doppler Signals: A Preliminary Study in Breast Tumors," Radiology, 1995, vol. 197, No. 1, pp. 39–43.

Kedar et al., "Microbubble Contrast Agent for Color Doppler US: Effect on Breast Masses," (work in progress), Radiology, Mar. 1996, vol. 198, No. 3, pp. 679–686.

Kelly et al., "Prostate Cancer and the Role of Color Doppler US," Radiology, 1993, vol. 189, No. 1, pp. 153–156.

Kremer et al., "Ultrasonic in Vivo and in Vitro Studies on the Nature of the Ureteral Jet Phenomenon," Radiology, 1982, vol. 142, No. 1, pp. 175–177.

Ladefoged et al., "Renal Blood Flow, Circulation Times and Vascular Volume in Normal Man Measured by the Intraarterial Injection—External Counting Technique," Acta Physiologica Scandinavica, 167, vol. 69, pp. 220–229.

Luker et al., "Pediatric Testicular Tumors: Evaluation with Gray–Scale and Color Doppler US," Radiology, 1994, vol. 191, No. 2, pp. 561–564.

Luker et al., "Scrotal US in Pediatric Patients: Comparison of Power and Standard Color Doppler US," Radiology, Feb. 1996, vol. 198, No. 2, pp. 381–385.

Newman et al., "Detection of Soft–Tissue Hyperemia: Value of Power Doppler Sonography," American Journal of Roentgenology, 1994, vol. 163, pp. 385–389.

Newman et al., "Prostate Cancer: Diagnosis with Color Doppler Sonography with Histoogic Correlation of Each Biopsy Site," Radiology, 1995, vol. 195, No. 1, pp. 86–90.

Newman et al., "Power Doppler Sonography of Synovitis: Assessment of Therapeutic Response —Preliminary Observations," Radiology, Feb. 1996, vol. 198, No 2, pp. 582–584.

Paulson et al., "Diagnosis of Acute Cholecystitis with Color Doppler Sonography: Significance of Arterial Flow in Thickened Gallbladder Wall," American Journal of Roentgenology, 1994, vol. 162, pp. 1105–1108.

Price et al., "Ultrasound Detection of Defferences in Density Explanation of the Ureteric Jet Phenomenon and Implications for New Ultrasound Applications," Investigative Radiology, 989, ol 24, No. 11, pp. 876–883.

Rempp et al., "Quantification of Regional Cerebral Blood Flow and Volume with Dynamic Susceptibility Contrast–Enhanced MR Imaging,"Radiology, 1994, vol. 193, No. 3, pp. 637–641.

Rifkin et al., "Prostate: Techniques, Results, and Potential Applications of Color Doppler US Scanning," Radiology, 1993, vol. 186, No. 2, pp. 509–513.

Rubin et al., "Fractional Moving Blood Volume: Estimation with Power Doppler US," Radiology, 995, vol. 197, No. 1, pp. 183–190.

Rubin et al., "Power Doppler US: A Potentially Useful Alternative to Mean Frequency–Based Color Doppler US" Radiology, 1994; vol. 190, No. 3, pp. 853–856.

Rubin et al., "Visualization of Tumor Vascularity in a Rabbit V 2 Carcinoma by Doppler FLow Mapping," Journal of Ultrasound Medicine, 1987, vol 6, No. 3, pp. 113–120.

Schrope et al., "Second Harmonic Ultrasonic Blood Perfusion Measurement,," Ultrasound in Medicine and Biology, vol. 19, No. 7, pp. 567–579.

Selkurt, "The Renal Circulation," Handbook of Physiology, Section 2: Circulation, vol. II, Hamilton et al., editors, Washington, DC: American Physiological Sociey, 1963, pp. 1457–1516.

Shiamoto et al., "Intratumoral Blood Flow: Evaluation with Color Doppler Echography," Radiology, 1987, vol. 165, No. 3, pp. 683–685.

Shmulewitz et al., "Temperature–Dependent Ultrasound Color Flow Doppler Imaging in the Study of a VX2 Tumor in Rabbits: Preliminary Findings," Ultrasound in Medicine and Biology, 1993, vol. 19, No. 3, pp. 221–229.

Shung et al., "The Effects of Hematocrit, Shear Rate, and Turbulence on Ultrasonic Doppler Spectrum from Blood," IEEE Transactions on Biomedical Engineering, 1992, vol. 39, No. 5, pp. 462–469.

Shung et al., "Ultrasound Scattering Properties of Blood, "Intravascular Ultrasound, Developments in Cardiovascular Medicine, Bom et al., editors, The Netherlands: Kluwer Academic Publishers, 1993, pp. 119–139.

Shung, "In Vitro Experimental Results on Ultrasonic Scattering in Biological Tissues," Ultrasonic Scattering in Biological Tissues, Shung et al., editors, Boca Raton, FL: CRC Press, 1993, pp. 291–312.

Sohn et al., "Die dopplersonographische Untersuchung von Mammatumoren mit Hilfe der Farbdopplersonographie, der Duplexsonographie und des CW–Dopplers" (English translation attached: Doppler Ultrasonographic Examinations of Breast Tumors Using Color Doppler, Duplex, and Continuous–Wave Doppler Ultrasonography), Zentralblatt für Gynäkologie, 1992, 114:249–253.

Tanaka et al., "Color Doppler Flow Imaging of Liver Tumors," American Journal of Roentgenology, 1990, vol. 154, pp. 509–514.

Teefey et al., "Bowel Wall Thickening: Differentiation of Inflammation from Ischemia with Color Doppler and Duplex US," Radiology, Feb. 1996, vol. 198, No. 2, pp. 547–551.

Watson et al.,"Contrast Agents," Magnetic Resonance Imaging, Stark et al., editors, St Louis, MO: Mosby Year Book, 1992, pp. 413–421.

Weidner et al., "Tumor Angiogenesis and Metastasis —Correlation in Invasive Breast Carcinoma," The New England Journal of Medicine, 1991, vol. 324, No. 1, pp. 1–8.

Wilson et al., "A Feasibility Study on Quantitating Myocardial Perfusion with Albunex, and Ultrasonic Contrast Agent," Ultrasound in Medicine and Biology, 1993; Vol. 19, No. 3, pp. 181–191.

5,860,929

FRACTIONAL MOVING BLOOD VOLUME ESTIMATION WITH POWER DOPPLER ULTRASOUND

The U.S. Government may have rights in this invention as provided by the terms of Grant Number ROI CA55076 awarded by the U.S. Public Health Service.

FIELD OF THE INVENTION

The invention relates in general to the field of medicine, and more particularly, to the use of power Doppler ultrasound in medical imaging. Specifically, the invention relates to methods of measuring the amount of moving blood in tissue in a region of interest.

BACKGROUND OF THE INVENTION

In the diagnosis of various medical conditions, it is often useful to examine soft tissues and/or blood flow within the body to show structural details of organs and blood vessels in these organs. Multiple studies have demonstrated increased vascularity (blood flow) in many tumors relative to that of normal tissue, and multiple attempts have been made to depict these differences in vascularity using ultrasonic imaging.

As well-known to those of ordinary skill, a standard real-time two-dimensional (2D) ultrasound scan typically entails the following. Referring to FIG. 1, an operator holds a transducer 105 in one position relative to a volume of material, e.g., human tissue in a patient 120. The transducer 105 is sometimes referred to as a scan head; it commonly has an essentially linear, one-dimensional (1D) shape, although scan heads of round or other shapes are also known, and emits a beam of ultrasound energy toward the material in a patient 120. The ultrasound energy is reflected from the material and detected by the scan head 105, which generates data signals representative of the detected energy.

A conventional ultrasound machine 100, operating under the control of a processor 102 such as a microprocessor, receives and processes the resulting data from the scan head 105. The processor 102 typically reads program instruction statements and/or data from a program storage device 101 such as read-only memory (ROM). The ultrasound machine 100 displays a 2D image of the tissue volume being scanned, e.g., on a video display terminal 110, a film camera, or other hard copy device (not shown). Movement of the scan head 105 results in different 2D views of the tissue volume being presented.

Additional background information can be found in, e.g., Fractional Moving Blood Volume: Estimation with Power Doppler US, at pages 183 et seq. of the October 1995 edition of RADIOLOGY, which is incorporated herein by reference, and in the references cited therein.

SUMMARY OF INVENTION

The invention describes a method for quantitatively estimating the amount of moving blood a tissue contains (fractional moving blood volume) for a given region of interest (ROI) using power Doppler ultrasound. A region of interest is identified from a frozen image (i.e., a snapshot screen display created by displaying the last real-time image for a given scan). The region of interest is specified by using a pointing device (e.g., a mouse). An object that contains one hundred percent blood flow, e.g., a blood vessel, and is located at the same depth as the region of interest, but not necessarily inside the region of interest, is identified and the corresponding power designated as the reference power level. The display is adjusted to show the vessel having one hundred percent blood flow in a designated color (such as, for example, green) and all other power levels are normalized to the reference power level. The fractional blood volume is quantitatively estimated by summing the normalized Doppler power levels and dividing the sum by the number of pixels inside the region of interest.

DETAILED DESCRIPTION OF SPECIFIC EMBODIMENTS

Illustrative embodiments of the invention are described below as it might be employed in the method of quantitatively estimating the fractional moving blood volume estimation with power Doppler ultrasound. In the interest of clarity, not all features of an actual implementation are described in this specification. It will, of course, be appreciated that in the development of any such actual embodiment numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill having the benefit of this disclosure.

Overview

Figure 1:
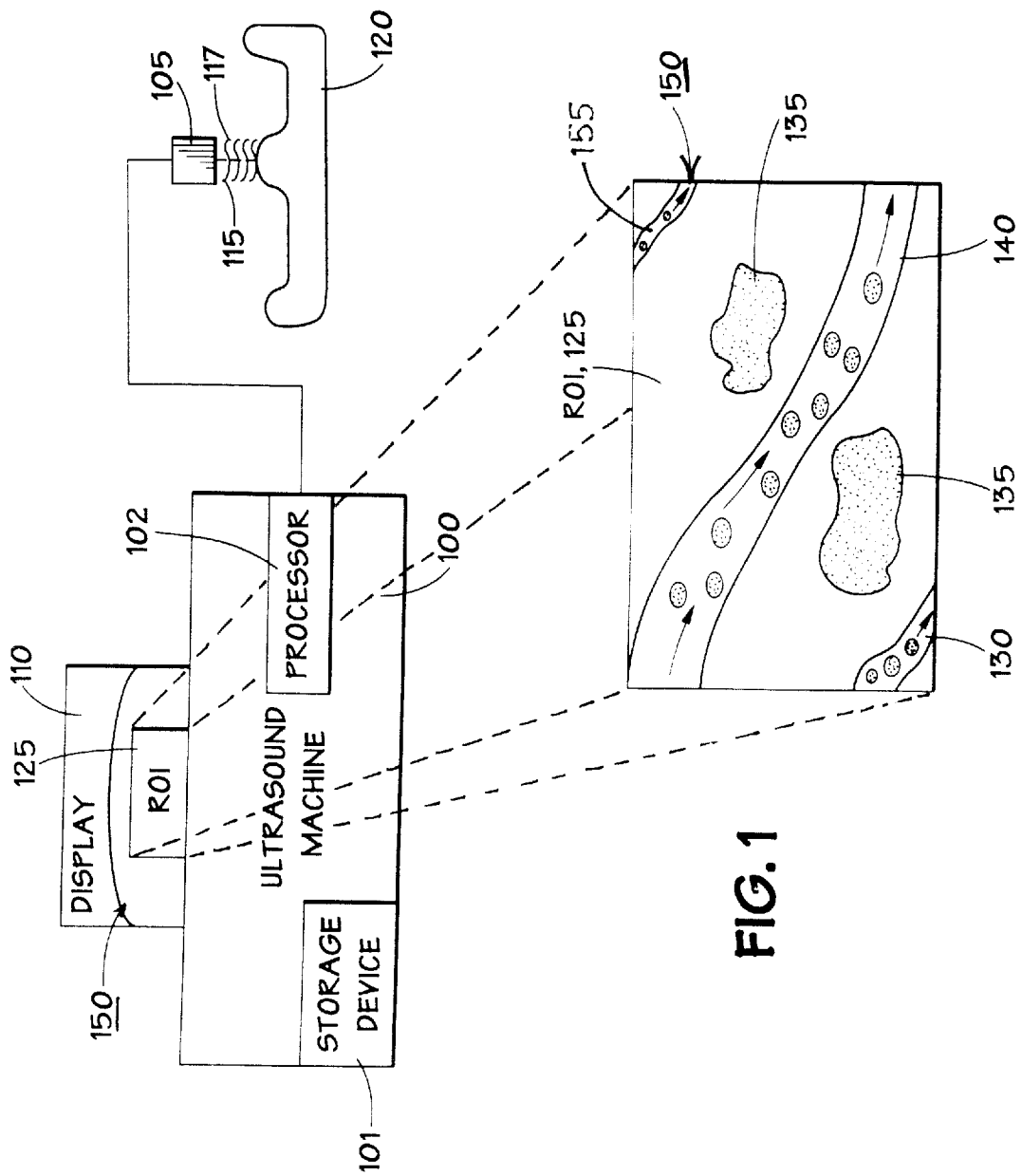
FIG. 1 illustrates the objects involved in acquiring a power Doppler image of targeted tissue.

FIG. 1 illustrates an schematic diagram of objects involved in acquiring a power Doppler ultrasound. The ultrasound machine 100 (e.g., a Spectra VST Scanner) contains both a display 110 and a scanning head 105. The scanning head may be movable to enable various regions of the scanning subject 120 to be imaged. The scanner 100 emits ultrasound signals (incident signals) 115 which are incident upon the scanning subject 120. Due to the variation of densities within the subject 120, the incoming signals 115 may become reflected signals 117, or echoes. The frequency differences between the incident signals 115 and the echoes 117 are analyzed by the ultrasound machine 100 to create an image 150.

Within an image 150, a region of interest (ROI) 125 may be designated. This region of interest 125 may contain several types of hard tissues (i.e., tissues in which no blood flows) 135. A region of interest 125 may also contain tissues through which varying amounts of blood flow like 130, 140 and 155. The invention provides a quantitative estimate for the amount of moving blood in tissue within the region of interest 125.

Specific Embodiments

Figure 2:
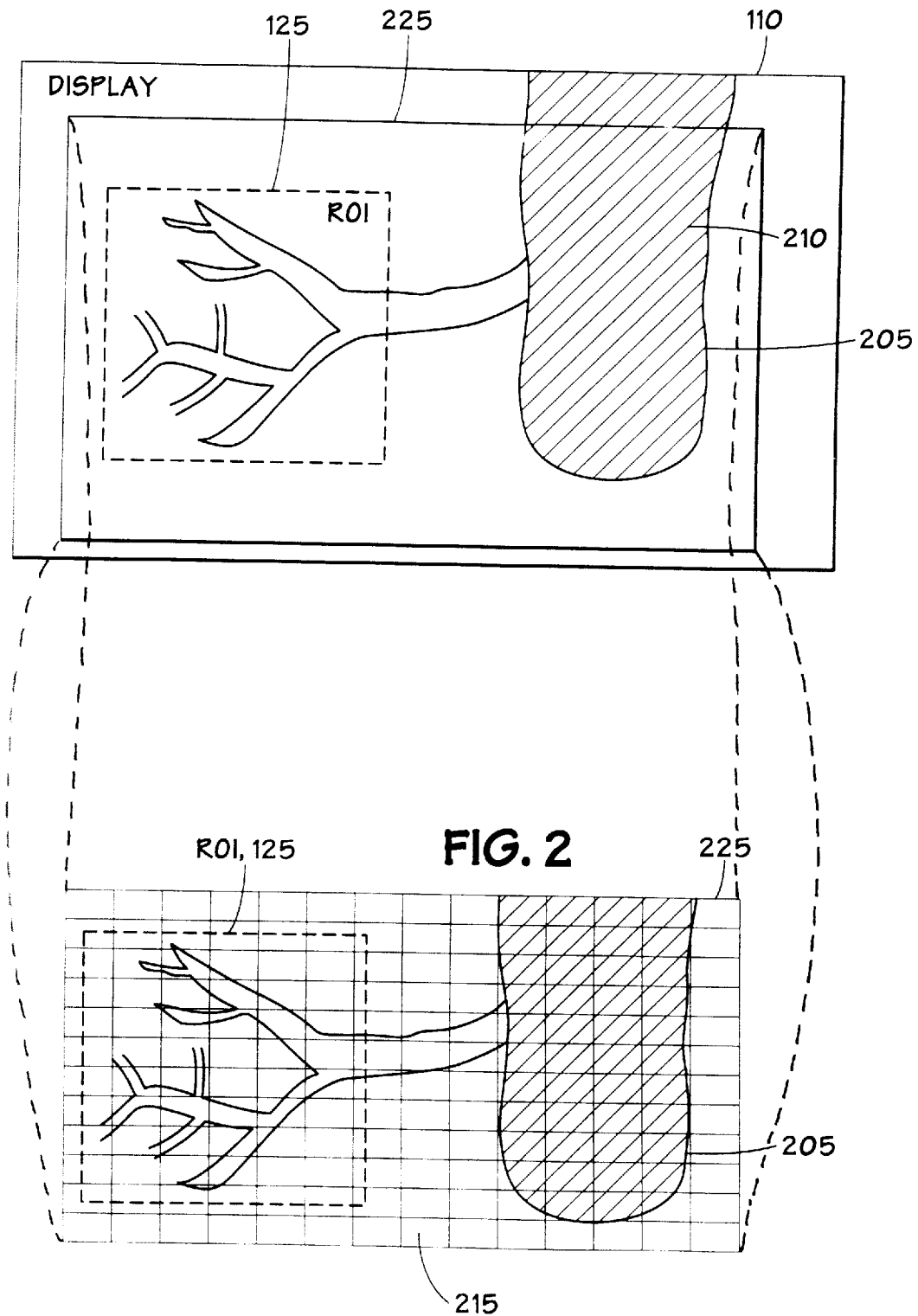
FIG. 2 illustrates specification of a region of interest and an associated reference vessel.

FIG. 2 shows an enlargement of a display 110 and a window 225 which is divided into squares or pixels 215. Since a region of interest 125 may contain multiple pixels 215, a summation may need to be performed to provide a quantitative answer. Ultrasound is attenuated with depth and therefore quantitative measurements made with ultrasound should be depth normalized. A reference vessel 205 containing 100 percent moving blood (e.g., a blood vessel) at the depth of the region of interest 125 may be used for normalization purposes. Normalization may be done on the display 110 by adjusting a color knob until the reference vessel 205 is approximately seventy five percent filled with a specified color 210 (e.g., green) and noting the corresponding power level (reference power level) which results in acceptable and nearly correct answers. If the depiction of the reference vessel 205 is less than about seventy five percent filled, the fractional moving blood volume is likely to be underestimated while completely filling the depiction of the reference vessel tends to overestimate the fractional moving blood volume. Hence, the judgment of the operator should be used to ensure proper normalization. This is colloquially referred to as "setting a green tag level." Any pixel value with a power level greater than the reference power level is set to the reference power level which ensures that the estimate of the fractional moving blood volume is never greater than one. Those of ordinary skill in the art will recognize that though the reference vessel 205 needs to be at the same depth in the tissue it need not necessarily be inside the region of interest 125. It will also be apparent to those of ordinary skill in the art having the benefit of this disclosure that an ultrasound contrast agent may be used instead of a reference vessel that contains a hundred percent moving blood to estimate the fractional moving blood volume.

Figure 3:
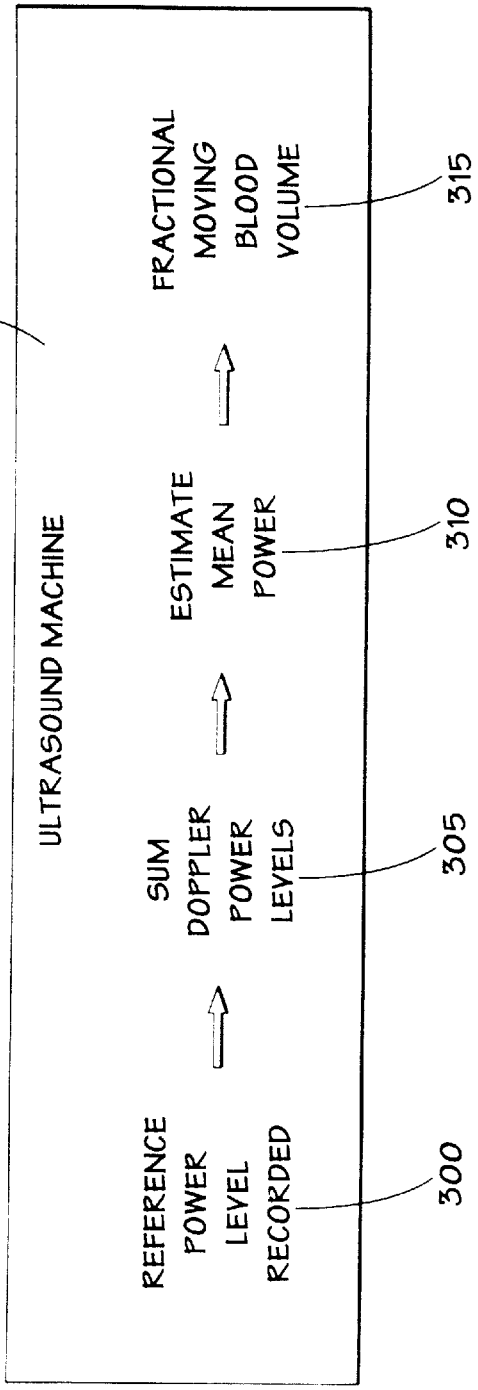
FIG. 3 is a flow chart that illustrates the actions performed by the ultrasound machine to generate an estimate of the fractional moving blood volume.

FIG. 3 illustrates the operations performed by the scanner once the reference power level (power level associated with the reference vessel) has been recorded at 300. Since each pixel 215 has a color associated with it and thus an associated power also, at 305 all of the power levels for each pixel 215 in the region of interest 125 are summed to yield the total power for the region of interest. At 310, an estimate of the mean power is calculated by dividing the total power for the region of interest by the number of pixels in the region of interest. A fractional moving blood volume for a given depth may be estimated at 315 by dividing the mean power estimate by the reference power level. The value of the fractional moving blood volume may then be shown on the display 110 or utilized in other calculations. It will be apparent to those of ordinary skill in the art having the benefit of this disclosure that a series of summations for a given region of interest may be used to yield a corresponding estimate of the fractional moving blood volume for any location in the subject 120.

Program Storage Device

Any of the foregoing variations may be implemented by programming a suitable ultrasound machine having an appropriate processor or processors 102. The programming may be accomplished through the use of a program storage device readable by the processor encoding a program of instructions executable by the machine for performing the operations described above. The program storage device may take the form of, e.g., one or more floppy disks; a CD ROM or other optical disk; a magnetic tape; a read-only memory chip (ROM); and other forms of the kind well-known in the art or subsequently developed. The program of instructions may be "object code," i.e., in binary form that is executable more-or-less directly by the computer; in "source code" that requires compilation or interpretation before execution; or in some intermediate form such as partially compiled code. The precise forms of the program storage device and of the encoding of instructions is immaterial here.

It will be appreciated by those of ordinary skill in the art having the benefit of this disclosure that numerous variations from the foregoing illustration will be possible without departing from the inventive concept described therein. Accordingly, it is the claims set forth below, and not merely the foregoing illustration, which are intended to define the exclusive rights claimed in this application.

What is claimed is:

1. A method of quantifying fractional moving blood volume in a tissue volume, said method comprising:
   (a) receiving a signal encoding a power Doppler scan of the tissue volume, said signal including a plurality of samples;
   (b) designating a region of interest at a selected depth within the tissue volume, said region of interest corresponding to a target portion of the signal;
   (c) identifying, in a reference portion of the signal received from a depth within the tissue volume substantially similar to the selected depth, a reference Doppler power level associated with 100% flow;
   (d) computing a mean power estimate by averaging respective target Doppler power levels of the samples in the target portion; and
   (e) computing a fractional moving blood volume estimate by normalizing the mean power estimate to the reference Doppler power level.

2. The method of claim 1, further including generating a visual display of the fractional moving blood volume estimate.

3. A method of quantifying fractional moving blood volume in a tissue volume, said method comprising:
   (a) performing a power Doppler scan of the tissue volume to generate an image of the tissue volume, said image including a plurality of pixels;
   (b) designating a region of interest at a selected depth within the tissue volume, said region of interest corresponding to a target portion of the image;
   (c) identifying, in a reference portion of the image received from a depth within the tissue volume substantially similar to the selected depth, a reference Doppler power level associated with 100% flow;
   (d) computing a mean power estimate equal to the sum of respective target Doppler power levels of pixels within the target portion divided by the number of said pixels within the target portion;
   (e) computing a fractional moving blood volume estimate by normalizing the mean power to the reference Doppler power level; and
   (f) generating a visual display of the fractional moving blood volume estimate.

4. The method of claim 3, wherein said target portion and said reference portion are disjoint sets of said plurality of pixels of said image, said disjoint sets having no common pixels common to both said target portion and said reference portion.

5. The method of claim 3, wherein said target portion and said reference portion include an overlapping portion of said image, said overlapping portion having at least one common pixel common to both said target portion and said reference portion.

6. The method of claim 5, wherein said overlapping portion of said image has a plurality of common pixels common to both said target portion and said reference portion.

7. The method of claim 6, wherein said plurality of common pixels includes substantially all of the pixels in said target portion.

8. The method of claim 6, wherein said plurality of common pixels includes substantially all of the pixels in said reference portion.

9. The method of claim 6, wherein said plurality of common pixels includes substantially all of the pixels in said target portion and in said reference portion.

10. An ultrasound machine comprising a signal input adapted to be coupled to an ultrasound scan head; a processor coupled to receive signals from the signal input; and a program storage device readable by the processor, tangibly embodying a program of instructions executable by the processor to perform the method of a specified one of claims 1 through 3.

11. A program storage device readable by a processor in an ultrasound machine, tangibly embodying a program of instructions executable by the processor to perform the method of a specified one of claims 1 through 3.

12. The method of claim 1, wherein said target portion and said reference portion are disjoint sets of said plurality of samples of said signal, said disjoint sets having no common samples common to both said target portion and said reference portion.

13. The method of claim 1, wherein said target portion and said reference portion include an overlapping portion of said signal, said overlapping portion having at least one common sample common to both said target portion and said reference portion.

14. The method of claim 13, wherein said overlapping portion of said signal has a plurality of common samples common to both said target portion and said reference portion.

15. The method of claim 14, wherein said plurality of common samples includes substantially all of the samples in said target portion.

16. The method of claim 14, wherein said plurality of common samples includes substantially all of the samples in said reference portion.

17. The method of claim 14, wherein said plurality of common samples includes substantially all of the samples in said target portion and in said reference portion.

18. The method of claim 1, wherein said reference Doppler power level associated with 100% flow is associated with a reference blood vessel having 100% flow and said fractional moving blood volume estimate is depth normalized to said selected depth.

19. The ultrasound machine of claim 10, wherein said program of instructions includes instructions for performing one of the method of claim 1 and a first specified one of claims 12 through 18, the method of claim 2 and a second specified one of claims 12 through 18, and the method of claim 3 and a third specified one of claims 14 through 9.

20. The program storage device of claim 11, wherein said program of instructions includes instructions for performing one of the method of claim 1 and a first specified one of claims 12 through 18, the method of claim 2 and a second specified one of claims 12 through 18, and the method of claim 3 and a third specified one of claims 4 through 9.

* * * * *